US010112982B2

(12) United States Patent
Miske et al.

(10) Patent No.: US 10,112,982 B2
(45) Date of Patent: Oct. 30, 2018

(54) DETECTION OF ANTI-NEUROCHONDRIN AUTOANTIBODY IN PATIENTS WITH CEREBELLAR ATAXIA OR CEREBELLITIS

(71) Applicant: EUROIMMUN MEDIZINISCHE LABORDIAGNOSTIKA AG, Luebeck (DE)

(72) Inventors: Ramona Miske, Luebeck (DE); Madeleine Scharf, Luebeck (DE); Lars Komorowski, Ratzeburg (DE); Yvonne Denno, Luebeck (DE); Christian Probst, Ratzeburg (DE); Inga-Madeleine Dettmann, Ahrensboek (DE); Winfried Stöcker, Gross Groenau (DE); Bianca Teegen, Rehna (DE); Nico Melzer, Muenster (DE); Heinz Wiendl, Muenster (DE); Sven Meuth, Muenster (DE)

(73) Assignee: EUROIMMUN MEDIZINISCHE LABORDIAGNOSTIKA AG, Luebeck (DE)

(*) Notice: Subject to any disclaimer, the term of this patent is extended or adjusted under 35 U.S.C. 154(b) by 0 days.

(21) Appl. No.: 15/078,361

(22) Filed: Mar. 23, 2016

(65) Prior Publication Data
US 2016/0311876 A1  Oct. 27, 2016

(30) Foreign Application Priority Data
Apr. 22, 2015 (EP) .................... 15001186

(51) Int. Cl.
A61K 49/00 (2006.01)
A61K 49/16 (2006.01)
C07K 14/00 (2006.01)
G01N 33/53 (2006.01)
G01N 33/567 (2006.01)
C07K 14/47 (2006.01)
G01N 33/68 (2006.01)
G01N 33/564 (2006.01)
C07K 16/18 (2006.01)
A61K 38/00 (2006.01)

(52) U.S. Cl.
CPC .......... C07K 14/4713 (2013.01); C07K 16/18 (2013.01); G01N 33/564 (2013.01); G01N 33/6896 (2013.01); A61K 38/00 (2013.01); C07K 2317/14 (2013.01); G01N 2333/47 (2013.01)

(58) Field of Classification Search
CPC .... A61K 38/00; C07K 14/4713; C07K 16/18; C07K 2317/14; C12Q 1/6886; C12Q 2600/158; G01N 2333/47; G01N 33/564; G01N 33/57415
See application file for complete search history.

(56) References Cited

U.S. PATENT DOCUMENTS

| 7,588,892 | B2* | 9/2009 | Natsoulis | G01N 33/6893 435/6.14 |
|---|---|---|---|---|
| 7,590,493 | B2* | 9/2009 | Mendrick | G01N 33/5014 435/6.16 |
| 2002/0119462 | A1* | 8/2002 | Mendrick | C12Q 1/6876 435/6.14 |
| 2003/0207394 | A1* | 11/2003 | Alsobrook, II | C07K 14/47 435/69.1 |
| 2004/0002067 | A1* | 1/2004 | Erlander | C12Q 1/6886 435/6.14 |
| 2006/0057066 | A1* | 3/2006 | Natsoulis | G01N 33/6893 424/9.1 |
| 2006/0141541 | A1 | 6/2006 | McIntyre | |
| 2006/0199205 | A1* | 9/2006 | Natsoulis | G01N 33/6893 435/6.18 |
| 2006/0234287 | A1* | 10/2006 | Erlander | C12Q 1/6886 435/6.14 |
| 2007/0093969 | A1* | 4/2007 | Mendrick | C12Q 1/6876 702/20 |
| 2007/0105105 | A1* | 5/2007 | Clelland | C12Q 1/6809 435/6.14 |
| 2007/0124086 | A1* | 5/2007 | Mendrick | C12Q 1/6876 702/20 |
| 2007/0224644 | A1* | 9/2007 | Liotta | C12Q 1/485 435/7.1 |
| 2011/0288011 | A1* | 11/2011 | Castaigne | A61K 47/48246 514/5.3 |
| 2014/0323391 | A1* | 10/2014 | Tsalik | C12Q 1/689 514/2.7 |

(Continued)

FOREIGN PATENT DOCUMENTS

WO 2008/148489 12/2008
WO 2008/148489 A1 12/2008

OTHER PUBLICATIONS

Pawson et al. 2003, Science 300:445-452.*
Bowie et al. Science, 1990, 247:1306-1310.*
Burgess et al. J of Cell Bio. 1990, 111:2129-2138.*
Manifava et al., Differential binding of traffic-related proteins to phosphatidic acid- or phosphatidylinositol (4,5)—bisphosphate-coupled affinity reagents, Journal of Biological Chemistry, American Society for Biochemistry and Molecular Biology, Mar. 23, 2001, pp. 8987-8994, XP002204100, ISSN: 0021-9258, DOI: 10.1074/JBC.M010308200.

(Continued)

Primary Examiner — Chang-Yu Wang
(74) Attorney, Agent, or Firm — Stoel Rives LLP; Zhi-Xiang (Alex) Oh

(57) ABSTRACT

Polypeptides including Neurochondrin and autoantibodies binding to polypeptides including Neurochondrin are provided. Methods for diagnosing or treating diseases associated with neurological symptoms or cancers are also provided. The methods of diagnosis may include detecting an autoantibody binding to Neurochondrin in a sample from a patient. The methods of treatment may include administering a polypeptide comprising Neurochondrin to a patient.

11 Claims, No Drawings
Specification includes a Sequence Listing.

(56) References Cited

U.S. PATENT DOCUMENTS

2016/0097099 A1* 4/2016 Tsalik .................... C12Q 1/689
424/569
2016/0263235 A1* 9/2016 Castaigne ........ A61K 47/48246

OTHER PUBLICATIONS

Zaenker et al., Serologic Autoantibodies as Diagnostic Cancer Biomarkers—A Review, Cancer Epidemiology, Biomarkers, & Prevention, Sep. 20, 2013, pp. 2161-2181, vol. 22, No. 12, XP055199823, ISSN: 1055-9965, DOI: 10.1158/1055-9965.EPI-13-0621.

Schwaibold et al., Identification of Neurochondrin as a new interaction partner of the FH3 domain of the Diaphanous-related formin Dia1, Biochemical and Biophysical Research Communications, Academic Press Inc., Aug. 29, 2008, pp. 366-372, vol. 373, No. 3, XP022939470, ISSN: 0006-291X, DOI: 10.1016/J.BBRC.2008.06.042.

Extended European Search Report received in EP application No. 15001186.4, dated Jul. 14, 2015.

Extended European Search Report dated Jul. 14, 2015 as received in European Patent Application No. 15001186.4.

Manifava et al., "Differential binding of traffic-related proteins to phosphatidic acid- or phosphatidylinositol (4,5)- biphosphate-coupled affinity reagents," Journal of Biological Society for Biochemistry and Molecular Biology, US, vol. 276, No. 12, Mar. 23, 2001, pp. 8987-8994, DOI: 10.1074/JBC.M0108200.

Zaenker et al., "Serologic Autoantibodies as Diagnostic Cancer Biomarkers—A Review," Cancer Epidemiology, Biomarkers & Prevention, vol. 22, No. 12, Sep. 20, 2013, pp. 2161-2181, DOI: 10.1158/1055-9965.EPI-13-0621.

Schwaibold et al., "Identification of Neurochondrin as a new itneraction partner of the FH3 domain of the Diaphanous-related formin Dia1," Biochemical and Biophysical Research Communications, Academic Press Inc. Orlando, FL, US, vol. 373, No. 3, Aug. 29, 2008, pp. 366-372, DOI: 10.1016/J.BBRC.2008.06.042.

Dateki et al., "Neurochondrin Negatively Regulates CaMKII Phosphorylation, and Nervous System-specific Gene Disruption Results in Epileptic Seizure," The Journal of Biological Chemistry, vol. 280, No. 21, Issue of May 27, pp. 20503-20508, 2005, U.S.A.

European Office Action dated Jul. 14, 2017 as received in European Application No. 15001186.4.

* cited by examiner

DETECTION OF ANTI-NEUROCHONDRIN AUTOANTIBODY IN PATIENTS WITH CEREBELLAR ATAXIA OR CEREBELLITIS

RELATED APPLICATIONS

This application claims the benefit of European Patent Application No. 15001186.4, filed Apr. 22, 2015, which is hereby incorporated by reference in its entirety.

SUMMARY

The present disclosure relates to methods for diagnosing a disease, for example, a disease associated with neurological symptoms and/or a cancer, comprising the step of detecting in a sample from a patient an autoantibody binding to Neurochondrin; polypeptides comprising Neurochondrin or variants thereof, which are immobilized, in some embodiments, on a solid carrier; uses of a polypeptide comprising Neurochondrin or a variant thereof for the diagnosis of a disease, in certain embodiments, comprising the step of detecting autoantibodies binding to Neurochondrin; polypeptides comprising Neurochondrin or variants thereof, in various embodiments, immobilized, in some embodiments, on a solid carrier, for use in the treatment of a disease; autoantibodies, in certain embodiments, an isolated autoantibody, binding to a polypeptide comprising Neurochondrin, wherein, in various embodiments, the autoantibody is in complex with said polypeptide or a variant thereof; methods for isolating an autoantibody binding to Neurochondrin, comprising the steps of: a) contacting a sample comprising the autoantibody with a polypeptide comprising Neurochondrin or a variant thereof under conditions compatible with formation of a complex, wherein said autoantibody binds to said polypeptide; b) isolating the complex formed in step a); c) dissociating the complex isolated in step b); and d) separating the autoantibody from the polypeptide; pharmaceutical compositions comprising a polypeptide comprising Neurochondrin or a variant thereof; medical or diagnostic devices comprising a polypeptide comprising Neurochondrin or a variant thereof; and test kits for the diagnosis of a disease, comprising a polypeptide comprising Neurochondrin or a variant thereof, wherein, in some embodiments, the test kit comprises, in addition, a means for detecting the complex comprising an autoantibody binding to Neurochondrin.

DETAILED DESCRIPTION

Developing diagnostic systems for neurological diseases is a continuing challenge in biomedical science, not in the least because many symptoms encountered may be accounted for by a huge variety of causes including genetically-inherited diseases, drug abuse, malnutrition, infection, injury, psychiatric illness, immunological defects and cancer.

Since a neurological disease is rarely associated with a unique characteristic pattern of clinical symptoms, it is often difficult to provide a reliable diagnosis solely based on the observation and examination of the patients affected or their medical history.

The importance of an early diagnosis cannot be overemphasized. Many neurological disorders, most prominently Alzheimer's and Parkinson's diseases, cannot be cured, but drugs are available that may be used to slow down their progression. The earlier the diagnosis, the better the chances to exploit the spectrum of available drugs to the full benefit of the patient.

This holds all the more true in the case of neurological diseases associated with autoantibodies. In some cases, the link between a specific detectable autoantibody and a condition is sufficiently strong to allow for an immediate diagnosis.

But even if it is not, the detection of autoantibodies may point the physician in charge to therapeutic means that may be used to ameliorate the patient's condition. There is a variety of widely used immunosuppressants that may be used regardless of the nature of the autoantibody's target. Alternatively, apheresis may be used to remove autoantibodies from the patient's blood. In many cases, patients went on to lead a normal life following early diagnosis and treatment of a neurological autoimmune disease.

Diagnostic assays based on the detection of autoantibodies may also corroborate the diagnosis of diseases other than those associated with autoantibodies. If it turns out that a blood sample is devoid of specific autoantibodies, this is likely to help the physician in charge exclude a range of possibilities and thus narrow down the spectrum of plausible conditions.

Examples of neurological conditions coinciding with the emergence of autoantibodies include *Neuromyelitis optica*, a disease characterized by loss of vision and spinal cord function, and anti-NMDA receptor encephalitis, which is associated with autonomic dysfunction, hypoventilation, cerebellar ataxia, hemiparesis, loss of consciousness, or catatonia. Whilst the involvement of autoantibodies and the nature of these conditions as such were previously poorly understood, many of these diseases can now be diagnosed and treated efficiently owing to the availability of assays based on the detection of autoantibodies.

Therefore, it is paramount that new approaches to distinguish neurological conditions associated with autoantibodies from those that are not be developed.

The problem underlying the present disclosure is to provide novel reagents, devices and methods that may be used to support the diagnosis and treatment of a neurological disease, in particular a neurological disease associated with one or more symptoms from the group comprising cerebrellar oculomotor disturbances, dysarthria, ataxia, asthenia, asynergy, delayed reaction time, dyschronometria, instability of gait, difficulty with eye movements, dysphagia, hypotonia, inflammatory cerebrospinal fluid changes, dysmetria and dydiadochokinesia.

Another problem underlying the present disclosure is to provide novel reagents, devices and methods that may be used to distinguish autoimmune diseases, in particular neurological autoimmune diseases, from diseases other than autoimmune diseases, not in the least for the purpose of determining the most promising treatment regimen for the patient affected, more specifically whether or not an immunosuppressive treatment is adequate.

The problem underlying the present disclosure is solved by the subject-matter of the attached independent and dependent claims.

In a first aspect, the problem underlying the present disclosure is solved by a method for diagnosing a disease, for example, a disease associated with neurological symptoms and/or a tumor, comprising the step of detecting in a sample from a patient an autoantibody binding to Neurochondrin.

In an embodiment of the first aspect, the sample is a bodily fluid comprising antibodies, for example, selected from the group comprising whole-blood, serum, cerebrospinal fluid and saliva.

In a second aspect, the problem underlying the present disclosure is solved by a polypeptide comprising Neurochondrin or a variant thereof, which is immobilized, for example, on a solid carrier.

In a third aspect, the problem underlying the present disclosure is solved by a use of a polypeptide comprising Neurochondrin or a variant thereof for the diagnosis of a disease, for example, comprising the step of detecting autoantibodies binding to Neurochondrin.

In a fourth aspect, the problem underlying the present disclosure is solved by a polypeptide comprising Neurochondrin or a variant thereof, for example, immobilized, for example, on a solid carrier, for use in the treatment of a disease.

In a fifth aspect, the problem underlying the present disclosure is solved by an autoantibody, for example, an isolated autoantibody, binding to a polypeptide comprising Neurochondrin, wherein the autoantibody is, for example, in complex with said polypeptide or a variant thereof.

In a sixth aspect, the problem underlying the present disclosure is solved by a method for isolating an autoantibody binding to Neurochondrin, comprising the steps of: a) contacting a sample comprising the autoantibody with a polypeptide comprising Neurochondrin or a variant thereof under conditions compatible with formation of a complex, wherein said autoantibody binds to said polypeptide; b) isolating the complex formed in step a); c) dissociating the complex isolated in step b); and d) separating the autoantibody from the polypeptide.

In a seventh aspect, the problem underlying the present disclosure is solved by a pharmaceutical composition comprising a polypeptide comprising Neurochondrin or a variant thereof.

In an eighth aspect, the problem underlying the present disclosure is solved by a medical or diagnostic device comprising a polypeptide comprising Neurochondrin or a variant thereof.

In an ninth aspect, the problem underlying the present disclosure is solved by a test kit for the diagnosis of a disease, for example, a disease associated with neurological symptoms and/or a cancer, which test kit comprises a polypeptide comprising Neurochondrin or a variant thereof, wherein, for example, the test kit comprises, in addition, a means for detecting the complex comprising an autoantibody binding to Neurochondrin or a variant thereof. In certain embodiments, the test kit is configured to detect the presence or absence of at least one complex comprising an autoantibody bound to (i) Neurochondrin or a variant thereof or (ii) a polypeptide comprising Neurochondrin or a variant thereof.

In an embodiment of any aspect or embodiment of the disclosure, the patient has or the disease is associated with one or more symptoms from the group comprising cerebrellar oculomotor disturbances, dysarthria, ataxia, asthenia, asynergy, delayed reaction time, dyschronometria, instability of gait, difficulty with eye movements, dysphagia, hypotonia, inflammatory cerebrospinal fluid changes, dysmetria and dydiadochokinesia, optionally further comprising cerebellar signal alterations, brainstem signal alterations, atrophy on magnetic resonance imaging and a cancer.

In an embodiment of any aspect or embodiment of the disclosure, the patient has or the disease is associated with one or more symptoms from the group comprising cerebrellar oculomotor disturbances, dysarthria and ataxia.

In an embodiment of any aspect or embodiment of the disclosure, the disease is associated with neurological or psychiatric symptoms and is, for example, a neurological autoimmune disease.

In an embodiment of any aspect or embodiment of the disclosure, the polypeptide is provided in the form of a cell comprising a nucleic acid encoding said polypeptide or in the form of a tissue comprising said polypeptide.

In an embodiment of any aspect or embodiment of the disclosure, the polypeptide is a recombinant and/or isolated polypeptide.

The present disclosure is based on the inventors' surprising finding that a neurological autoimmune disease exists that is associated with autoantibodies to Neurochondrin (NCDN) and symptoms from the group comprising cerebrellar oculomotor disturbances, dysarthria, ataxia, asthenia, asynergy, delayed reaction time, dyschronometria, instability of gait, difficulty with eye movements, dysphagia, hypotonia, inflammatory cerebrospinal fluid changes, dysmetria and dydiadochokinesia.

Furthermore, the present disclosure is based on the inventors' surprising finding that autoantibodies to NCDN exist and may be detected in samples from a number of patients suffering from neurological symptoms, but not in samples obtained from healthy subjects. Without wishing to be bound to any theory, the presence of such autoantibodies suggests that activity and function NCDN and/or downstream effectors is impaired in patients having NCDN autoantibodies to the effect that neurological symptoms occur.

NCDN is a 75 k Da protein which is evolutionarily conserved from invertebrates to vertebrates. The orthologous rat, murine and human proteins have an amino acid identity of 98%.

NCDN is rich in α-helices (65%) which are organized as tandem repeats. The protein was found to interact with several membrane proteins from the brain, including Sema4C, MCHR1 and GRM5. These interactions involve the C-terminal part of NCDN and the membrane-proximal region of the respective membrane proteins (Francke F., Ward R. J., Jenkins L., Kellett E., Richter D., Milligan G. and Bachner D., 2006, Interaction of neurochondrin with the melanin-concentrating hormone receptor 1 interferes with G protein-coupled signal transduction but not agonist-mediated internalization, The Journal of biological chemistry, 281, 43, 32496-32507; Wang H., Westin L., Nong Y., Birnbaum S., Bendor J., Brismar H., Nestler E., Aperia A., Flajolet M. and Greengard P., 2009, Norbin is an endogenous regulator of metabotropic glutamate receptor 5 signaling, Science (New York, N.Y.), 326, 5959, 1554-1557).

NCDN was found to induce neurite outgrowth when ectopically overexpressed in cultured neuroblastoma N2a cells. It was shown that NCDN recruits Dia, an actin nucleation factor that stimulates barbed end actin filament elongation to a specific sub-cellular localization. This recruitment contributes to neurite-outgrowth function of NCDN (Schwaibold E. M. and Brandt D. T., 2008, Identification of Neurochondrin as a new interaction partner of the FH3 domain of the Diaphanous-related formin Dia1, Biochem Biophys Res Commun, 373, 3, 366-372).

NCDN modulates the signaling pathway of GRM5 (Wang H., Westin L., Nong Y., Birnbaum S., Bendor J., Brismar H., Nestler E., Aperia A., Flajolet M. and Greengard P., 2009, Norbin is an endogenous regulator of metabotropic glutamate receptor 5 signaling, Science (New York, N.Y.), 326, 5959, 1554-1557). GRM5 primarily responds to the excitatory amino acid neurotransmitter glutamate, localizes at perisynaptic sites and plays important roles in normal brain function as well as in several pathological disorders including schizophrenia (Abe T., Sugihara H., Nawa H., Shigemoto R., Mizuno N. and Nakanishi S., 1992, Molecular characterization of a novel metabotropic glutamate receptor mGluR5 coupled to inositol phosphate/Ca2+ signal transduction, The Journal of biological chemistry, 267, 19, 13361-13368, Romano C., Sesma M. A., McDonald C. T., O'Malley K., Van den Pol A. N. and Olney J. W., 1995, Distribution of metabotropic glutamate receptor mGluR5 immunoreactivity in rat brain, The Journal of comparative neurology, 355, 3, 455-469, Nakanishi S., Nakajima Y., Masu M., Ueda Y., Nakahara K., Watanabe D., Yamaguchi S., Kawabata S. and Okada M., 1998, Glutamate receptors: brain function and signal transduction, Brain research Brain research reviews, 26, 2-3, 230-235, Conn P. J., Christopoulos A. and Lindsley C. W., 2009, Allosteric modulators of GPCRs: a novel approach for the treatment of CNS disorders, Nature reviews Drug discovery, 8, 1, 41-54). NCDN expression enhances GRM5 signaling in an in vitro expression system, while the conditional knockout of NCDN in transgenic mice reduces GRM5 function. In line with reduced GRM5 function, NCND knockout mice show defects in pre-pulse inhibition and psychostimulant induced locomotor activity, two behavioral phenotypes typically observed in rodent models of schizophrenia (Wang H., Westin L., Nong Y., Birnbaum S., Bendor J., Brismar H., Nestler E., Aperia A., Flajolet M. and Greengard P., 2009, Norbin is an endogenous regulator of metabotropic glutamate receptor 5 signaling, Science (New York, N.Y.), 326, 5959, 1554-1557).

NCDN has been shown to inhibit MCHR-induced G-protein activation and downstream calcium influx. MCHR1 is the melanin-concentrating hormone receptor involved in the regulation of feeding behavior and energy balances (Lembo P. M., Grazzini E., Cao J., Hubatsch D. A., Pelletier M., Hoffert C., St-Onge S., Pou C., Labrecque J., Groblewski T., O'Donnell D., Payza K., Ahmad S. and Walker P., 1999, The receptor for the orexigenic peptide melanin-concentrating hormone is a G-protein-coupled receptor, Nature Cell biology, 1, 5, 267-271).

NCDN is a negative regulator of Ca2+/calmodulin-dependent protein kinase II (CaMKII) (Thr286) phosphorylation and essential for the spatial learning process but not for the differentiation or neurite outgrowth of the neuron. In addition, nervous system-specific homozygous gene disruption resulted in epileptic seizure (Dateki M., Horii T., Kasuya Y., Mochizuki R., Nagao Y., Ishida J., Sugiyama F., Tanimoto K., Yagami K., Imai H. and Fukamizu A., 2005, Neurochondrin negatively regulates CaMKII phosphorylation, and nervous system-specific gene disruption results in epileptic seizure, The Journal of biological chemistry, 280, 21, 20503-20508).

The present disclosure relates to a polypeptide comprising a mammalian, for example, human NCDN or variants thereof, for example, immunogenic variants binding to NCDN autoantibodies. In an embodiment, the polypeptide comprises NCDN as encoded by the data base code Q9UBB6 or a variant thereof. Throughout this application, any data base codes cited refer to the Uniprot data base, more specifically the version accessible on-line on Apr. 17, 2015. SEQ ID NO:1 represents a nucleotide sequence encoding NCDN. In an embodiment, the polypeptide comprises an amino acid sequence selected from the group comprising SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

The teachings of the present disclosure may not only be carried out using polypeptides, in particular a polypeptide comprising the native sequence of NCDN, or nucleic acids having the exact sequences referred to in this application explicitly, for example, by function, name, sequence or accession number, or implicitly, but also using variants of such polypeptides or nucleic acids.

In an embodiment, the term "variant," as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150 or 200 successive amino acids of the original sequence or a variant thereof. The total length of the variant may be at least 6, 7, 8, 9, 10, 11, 12, 20, 25, 30, 40, 50, 60, 70, 80, 90, 100 or more amino acids.

In another embodiment, the term "variant" relates not only to at least one fragment, but also to a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example, the ability of an antigen to bind to an (auto) antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see, for example, Arthur Lesk (2008), Introduction to bioinformatics, Oxford University Press, 2008, 3rd edition. In an embodiment, the Clustal W software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings.

In an embodiment, variants may, in addition, comprise chemical modifications, for example, isotopic labels or covalent modifications such as glycosylation, phosphorylation, acetylation, decarboxylation, citrullination, hydroxylation and the like. The person skilled in the art is familiar with methods to modify polypeptides. Any modification is designed such that it does not abolish the biological activity of the variant.

Moreover, variants may also be generated by fusion with other known polypeptides or variants thereof and comprise active portions or domains, for example, having a sequence identity of at least 70, 75, 80, 85, 90, 92, 94, 95, 96, 97, 98 or 99% when aligned with the active portion of the reference sequence, wherein the term "active portion," as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In an embodiment, the term "variant" of a nucleic acid comprises nucleic acids the complementary strand of which hybridizes, for example, under stringent conditions, to the reference or wild type nucleic acid. Stringency of hybridization reactions is readily determinable by one of ordinary skilled in the art, and in general is an empirical calculation dependent on probe length, washing temperature and salt concentration. In general, longer probes require higher temperatures for proper annealing, while shorter probes less so. Hybridization generally depends on the ability of denatured DNA to reanneal to complementary strands present in an environment below their melting temperature: the higher the degree of desired homology between the probe and hybridizable sequence, the higher the relative temperature which may be used. As a result, higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In an embodiment, stringent conditions are applied for any hybridization, i.e., hybridization occurs only if the probe is 70% or more identical to the target sequence. Probes having a lower degree of identity with respect to the target sequence may hybridize, but such hybrids are unstable and will be removed in a washing step under stringent conditions, for example, lowering the concentration of salt to 2×SSC or, optionally and subsequently, to 0.5×SSC, while the temperature is, for example, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In an embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In an embodiment, the term variant of a nucleic acid sequence, as used herein, refers to any nucleic acid sequence that encodes the same amino acid sequence and variants thereof as the reference nucleic acid sequence, in line with the degeneracy of the genetic code.

The variant of the polypeptide has biological activity. In an embodiment, such biological activity is the ability to bind specifically to the NCDN autoantibodies found in patients suffering from the disease identified by the inventors.

The disclosed polypeptide, which comprises NCDN or a variant thereof, when used to carry out the teachings of the present disclosure, may be provided in any form and at any degree of purification, from tissues or cells comprising said polypeptide in an endogenous form, for example, cells overexpressing the polypeptide, crude or enriched lysates of such cells, to purified and/or isolated polypeptide which is essentially pure. In an embodiment, the polypeptide is a native polypeptide, wherein the term "native polypeptide," as used herein, refers to a folded polypeptide, for example, to a folded polypeptide purified from tissues or cells, for example, from mammalian cells or tissues, optionally from non-recombinant tissues or cells. In another embodiment, the polypeptide is a recombinant protein, wherein the term "recombinant," as used herein, refers to a polypeptide produced using genetic engineering approaches at any stage of the production process, for example, by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example, Handbooks "Strategies for Protein Purification," "Antibody Purification," "Purifying Challenging Proteins," "Recombinant Protein Purification," "Affinity Chromatography," "Ion Exchange Chromatography," "Gel Filtration (Size Exclusion Chromatography)," "Hydrophobic Interaction Chromatography," "Multimodal Chromatography" (2009/2010), published by GE Healthcare Life Sciences, and in Burgess, R. R., Deutscher, M. P. (2009), Guide to Protein Purification). In an embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection.

If the disclosed polypeptide comprising NCDN or a variant thereof is provided in the form of tissue, in some embodiments, the tissue is mammalian tissue, for example, human, rat, primate, donkey, mouse, goat, horse, sheep, pig or cow, for example, brain tissue. If a cell lysate is used, in some embodiments, the cell lysate comprises the membranes associated with the surface of the cell. If said polypeptide is provided in the form of a recombinant cell, in some embodiments, the recombinant cell is a eukaryotic cell such as a yeast cell, for example, a cell from a multicellular eukaryote such as a plant, mammal, frog or insect, for example, from a mammal, for example, rat, human, primate, donkey, mouse, goat, horse, sheep, pig or cow. For example, the cell may be a HEK293 cell transfected with a nucleic acid functionally encoding the disclosed polypeptide. The person skilled in the art is familiar with methods for preparing, transfecting and culturing such cells, for example, those described in Phelan, M. C. (2001), Basic Techniques in Mammalian Cell Tissue Culture, John Wiley.

The polypeptide used to carry out the disclosed teachings, including any variants, may be designed such that it comprises epitopes recognized by and/or binds specifically to autoantibodies binding to NCDN. In one embodiment, such polypeptide comprises a stretch of 6, 7, 8, 9, 10, 11, 12, 20, 25, 30, 40, 50, 60, 70, 80, 90, 100 or more, for example, at least 9 but no more than 16, consecutive amino acids from NCDN. The person skilled in the art is familiar with guidelines used to design peptides having sufficient immunogenicity, for example, those described in Jackson, D. C., Fitzmaurice, C. J., Brown, L. E., Zeng, W. (1999), Preparation and properties of totally synthetic immunogens, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173. Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) it has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example, those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71.

The disclosed polypeptide, which comprises NCDN or a variant thereof, when used according to the present disclosure, may be provided in any kind of conformation. For example, the polypeptide may be an essentially unfolded, a partially or a fully folded polypeptide. In an embodiment, the polypeptide is folded in the sense that the epitopes essential for the binding to the disclosed autoantibody, or the protein or variant thereof in its entirety, adopt the fold adopted by the native protein in its natural environment. The person skilled in the art is familiar with methods suitable to determine whether or not a polypeptide is folded and if it is, which structure it has, for example, limited proteolysis, NMR spectroscopy, CD spectroscopy or X-ray crystallography (see, for example, Banaszak L. J. (2008), Foundations of Structural Biology, Academics Press, or Teng Q. (2013), Structural Biology: Practical Applications, Springer), for example, multidimensional NMR spectroscopy is used.

The disclosed polypeptide may be a fusion protein which comprises amino acid sequences other than those taken from NCDN, in particular a C-terminal or N-terminal tag, for example, a C-terminal tag, which is, in an embodiment, as used herein, an additional sequence motif or polypeptide having a function that has some biological or physical function and may, for example, be used to purify, immobilize, precipitate or identify the disclosed polypeptide. In an embodiment, the tag is a sequence or domain capable of binding specifically to a ligand, for example, a tag selected from the group comprising His tags, thioredoxin, maltose binding protein, glutathione-S-transferase, a fluorescence tag, for example, from the group comprising green fluorescent protein.

The disclosed polypeptide may be an immobilized polypeptide. In an embodiment, the term "immobilized," as used herein, refers to a molecule bound to a solid carrier insoluble in an aqueous solution, for example, via a covalent bond, electrostatic interactions, encapsulation or entrapment, for example, by denaturing a globular polypeptide in a gel, or via hydrophobic interactions, for example, via one or more covalent bonds. Various suitable carriers, for example, paper, polystyrene, metal, silicon or glass surfaces, microfluidic channels, membranes, beads such as magnetic beads, column chromatography media, biochips, polyacrylamide gels and the like have been described in the literature, for example, in Kim, D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example, by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example, a bond formed by reaction of an epoxide group and an amine group as frequently used to couple lysine side chains to affinity columns.

The protein may be indirectly immobilized, for example, by immobilizing an antibody or other entity having affinity to the molecule, followed by formation of a complex to the effect that the molecule-antibody complex is immobilized. Various ways to immobilize molecules are described in the literature, for example, in Kim, D., Herr, and A. E. (2013), Protein immobilization techniques for microfluidic assays, Biomicrofluidics 7(4), 041501. In addition, various reagents and kits for immobilization reactions are commercially available, for example, from Pierce Biotechnology.

It is essential that the sample used for the diagnosis in line with the present disclosure comprises antibodies, also referred to as immunglobulins. Typically the sample of a bodily fluid comprises a representative set of the entirety of the subject's immunglobulins. However, the sample, once provided, may be subjected to further processing which may include fractionation, centrifugation, enriching or isolating the entirety of immunglobulins or any immunglobulin class of the subject, which may affect the relative distribution of immunglobulins of the various classes.

The reagents, devices, methods and uses described throughout this application may be used for the diagnosis of a disease. In an embodiment, the disease is a neurological disease. In an embodiment, the term "neurological disease," as used herein, refers to any disease associated with a defect of the nervous system, for example, the central nervous system, for example, the brain.

In an embodiment, the disease is a disease, for example, a neurological disease, associated with one or more symptoms, for example, two or more, for example, three or more from the group comprising cerebrellar oculomotor disturbances, dysarthria, ataxia, asthenia, asynergy, delayed reaction time, dyschronometria, instability of gait, difficulty with eye movements, dysphagia, hypotonia, inflammatory cerebrospinal fluid changes, dysmetria and dydiadochokinesia, optionally further comprising cerebellar signal alterations, brainstem signal alterations, atrophy on magnetic resonance imaging and a tumor/cancer.

In another embodiment, the disease is a neurological disease selected from the group comprising Alzheimer's Disease, Autism, Asperger's Syndrome, Apraxia, Aphasia, Cerebellar syndrome, Cerebellitis, Chorea, Encephalitis, Movement disorder, spinocerebellar ataxia, for example, a non-progressive form, Paralysis, Paraplegia, Gaucher's disease, Myopathy, Myasthenia gravis, Multiple Sclerosis, Parkinsons's disease, Polyneuropathy and Dementia, for example, Cerebellar syndrome, Cerebellitis, Movement disorder and Dementia.

In another embodiment, the disease is a cancer or, for example, paraneoplastic neurological syndrome, which is associated both with one or more neurological symptoms, for example, from the group comprising cerebrellar oculomotor disturbances, dysarthria, ataxia, asthenia, asynergy, delayed reaction time, dyschronometria, instability of gait, difficulty with eye movements, dysphagia, hypotonia, inflammatory cerebrospinal fluid changes, dysmetria and dydiadochokinesia, optionally further comprising cerebellar signal alterations, brainstem signal alterations, and atrophy on magnetic resonance imaging and is furthermore associated with a cancer. Detection of autoantibodies to Neurochrondrin may indicate an increased likelihood that a cancer is present which cannot be detected using other methods, or will appear as the disease progresses. In an embodiment, the cancer is a cancer of tumor selected from the group comprising tumor of the lung, tumor of the thymus, thymic tumor, testicular tumor, head and neck cancer tumor, breast cancer tumor, ano-genital cancer tumor, melanoma, sarcoma, carcinoma, lymphoma, leukemia, mesothelioma, glioma, germ cell tumor, choriocarcinoma, pancreatic cancer, ovarian cancer, gastric cancer, carcinomatous lesion of the pancreas, pulmonary adenocarcinoma, colorectal adenocarcinoma, pulmonary squamous adenocarcinoma, gastric adenocarcinoma, ovarian surface epithelial neoplasm (e.g., a benign, proliferative or malignant variety thereof), oral squamous cell carcinoma, non small-cell lung carcinoma, endometrial carcinoma, a bladder cancer, prostate carcinoma, acute myelogenous leukemia (AML), myelodysplasia syndrome (MDS), non-small cell lung cancer (NSCLC), Wilms' tumor, leukemia, lymphoma, desmoplastic small round cell tumor, mesothelioma (e.g., malignant mesothelioma), a gastric cancer, colon cancer, lung cancer, breast cancer, germ cell tumor, ovarian cancer, uterine cancer, thyroid cancer, hepatocellular carcinoma, thyroid cancer, liver cancer, renal cancer, kaposis, sarcoma, and another carcinoma or sarcoma. In an embodiment, the cancer is a gynecological cancer, for example, a uterine cancer.

In an embodiment, the term "diagnosis," as used herein, refers to any kind of procedure aiming to obtain information instrumental in the assessment whether a patient suffers or is likely or more likely than the average or a comparative subject, the latter, for example, having similar symptoms, to suffer from certain a disease or disorder in the past, at the time of the diagnosis or in the future, to find out how the disease is progressing or is likely to progress in the future or to evaluate the responsiveness of a patient with regard to a certain treatment, for example, the administration of immunosuppressive drugs. In other words, the term "diagnosis" comprises not only diagnosing, but also prognosticating and/or monitoring the course of a disease or disorder.

In many cases the mere detection, in other words determining whether or not detectable levels of the antibody are present in the sample, is sufficient for the diagnosis. If the autoantibody can be detected, this will be information instrumental for the clinician's diagnosis and indicates an increased likelihood that the patient suffers from a disease. In an embodiment, the relative concentration of the antibody in the serum, compared to the level that may be found in the average healthy subject, may be determined. While in many cases it may be sufficient to determine whether or not autoantibodies are present or detectable in the sample, the method carried out to obtain information instrumental for the diagnosis may involve determining whether the concentration is at least 0.1, for example, 0.2, 0.5, 1, 2, 5, 10, 20, 25, 50, 100, 200, 500, 1000, 10000 or 100000 times higher than the concentration found in the average healthy subject.

The person skilled in the art will appreciate that a clinician does usually not conclude whether or not the patient suffers or is likely to suffer from a disease, condition or disorders solely on the basis of a single diagnostic parameter, but needs to take into account other aspects, for example, the presence of other autoantibodies, markers, blood parameters, clinical assessment of the patient's symptoms or the results of medical imaging or other non-invasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another. In an embodiment, the meaning of any symptoms or diseases referred to throughout this application is in line with the person skilled in the art's understanding as of Apr. 17, 2015 as evidenced by text books and scientific publications.

Therefore, the term "diagnosis" does not, for example, imply that the diagnostic methods or agents according to the present disclosure will be definitive and sufficient to finalize the diagnosis on the basis of a single test, let alone parameter, but may refer to a contribution to what is referred to as a "differential diagnosis," i.e., a systematic diagnostic procedure considering the likelihood of a range of possible conditions on the basis of a range of diagnostic parameters. Consequently, the disclosed method, polypeptide or use, optionally for determining whether a patient suffers from the a disease, may comprise obtaining a sample from a patient, for example, a human patient, determining whether an autoantibody binding to NCDN is present in said sample, wherein said determining is performed by contacting the sample with the disclosed polypeptide and detecting whether binding occurs between said polypeptide and said autoantibody, for example, using a labeled secondary antibody, for example, using a method from the group comprising radioimmunoassay, Western blot, line blot, ELISA, indirect and immunofluorescence, wherein said autoantibody binds to said polypeptide if present in the sample, and diagnosing the patient as suffering or being more likely to suffer from said neurological disorder or cancer if the autoantibody was determined to be present in the sample.

The term "diagnosis" may also refer to a method or agent used to distinguish between two or more conditions associated with similar or identical symptoms.

The term "diagnosis" may also refer to a method or agent used to choose the most promising treatment regime for a patient. In other words, the method or agent may relate to selecting a treatment regimen for a subject. For example, the detection of autoantibodies may indicate that an immunosuppressive therapy is to be selected, which may include administrating to the patient one or more immunosuppressive drugs.

The present disclosure relates to a complex comprising an antibody, for example, autoantibody, binding to the disclosed polypeptide. Such a complex may be used or detected as part of a method for diagnosing a disease. A liquid sample comprising antibodies from a subject may be used to practice the method. Such a liquid sample may be any bodily fluid comprising a representative set of antibodies from the subject, for example, a sample comprising antibodies of the IgG immunglobulin class from the subject. For example, a sample may be cerebrospinal fluid (CSF), blood or blood serum, lymph, interstitial fluid and is, for example, serum or CSF, for example, serum.

The step of contacting a liquid sample comprising antibodies with the disclosed polypeptide may be carried out by incubating an immobilized form of said polypeptide in the presence of the sample comprising antibodies under conditions that are compatible with the formation of the complex comprising said polypeptide and an antibody, for example, an autoantibody, binding to the disclosed polypeptide. The liquid sample, then depleted of antibodies binding to the disclosed polypeptide may be removed subsequently, followed by one or more washing steps. Finally the complex comprising the antibody and the polypeptide may be detected. In an embodiment, the term "conditions compatible with the formation of the complex" are conditions that allow for the specific antigen-antibody interactions to build up the complex comprising the polypeptide an the antibody. In an embodiment, such conditions may comprise incubating the polypeptide in sample diluted 1:100 in PBS buffer for 30 minutes at 25° C. In an embodiment, the term "autoantibody," as used herein, refers to an antibody binding specifically to an endogenous molecule of the animal, for example, mammal, which produces said autoantibody, wherein the level of such antibody is, for example, elevated compared the average of any other antibodies binding specifically to such an endogenous molecule. In an embodiment, the autoantibody is an autoantibody binding to NCDN. Such an autoantibody may be isolated from samples taken from patients suffering from the neurological disorder characterized by two or more, for example, all symptoms selected from the group comprising mixed movement disorder, acute decline of visual performance, dysarthria and dysphagia.

In an embodiment, the detection of the complex for the prognosis, diagnosis, methods or test kit according to the present disclosure comprises the use of a method selected from the group comprising immunodiffusion techniques, immunoelectrophoretic techniques, light scattering immunoassays, light scattering immunoassays, agglutination techniques, labeled immunoassays such as those from the group comprising radiolabeled immunoassay, enzyme immunoassays, chemiluminscence immunoassays, and immunofluorescence techniques. The person skilled in the art is familiar with these methods, which are also described in the state of the art, for example, in Zane, H. D. (2001), Immunology—Theoretical & Practical Concepts in Laboratory Medicine, W. B. Saunders Company, in particular in Chapter 14.

Alternatively, a sample comprising tissue comprising the disclosed polypeptide rather than a liquid sample may be used. The tissue sample is, for example, from a tissue expressing endogenous NCDN. Such a sample, which may be in the form of a tissue section fixed on a carrier, for example, a glass slide for microscopic analysis, may then be contacted with the disclosed antibody, for example, autoantibody, binding to the disclosed polypeptide. The antibody is, for example, labeled to allow for distinction from endogenous antibodies binding to the disclosed polypeptide, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and the disclosed polypeptide may be correlated with reference data. For example, detection of said complex indicates that the patient who provided the sample analyzed has suffered, is suffering or is likely to suffer in the future from a disease. If a patient has been previously diagnosed and the method for obtaining diagnostically relevant information is run again, the amount of complex detected in both runs may be correlated to find out about the progression of the disease and/or the success of a treatment. For example, if the amount of complex is found to increase, this suggests that the disorder is progressing, likely to manifest in the future and/or that any treatment attempted is unsuccessful.

In an embodiment, a microplate, membrane ELISA, dot blot, or line blot is used to carry out the diagnostic method according to the disclosure. The person skilled in the art is familiar with the experimental setup, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; W02013041540). Briefly, the one or more antigen of interest, in the case of the present disclosure the disclosed polypeptide, may be attached to a carrier, for example, nitrocellulose membrane, often in combination with additional antigens and controls. The nitrocellulose carrier is subsequently exposed to a sample comprising antibodies such as diluted serum. If the sample comprises an antibody binding to the antigen, a complex is formed which may be detected, for example, by incubation with a secondary antibody binding to the constant region of the first antibody, which secondary antibody comprises a detectable label, for example, a radioactive isotope, a fluorescent dye or, in an embodiment, an active enzyme fused or linked to the secondary antibody, such as alkaline phosphatase, which may be readily assayed using chromogenic substrates followed by simple visual examination.

In another embodiment, the prognosis, diagnosis, methods or test kit in line with the disclosed teachings contemplate the use of indirect immunofluorescence. The person skilled in the art is familiar with such techniques and the preparation of suitable samples, which are described in the state of the art (U.S. Pat. No. 4,647,543; Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), "Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007). Briefly, a carrier, such as a cover glass for use in microscopy, is coated with cells or tissue sections comprising the antigen, in the case of the present disclosure the polypeptide comprising one or more sequences of NCDN or a variant thereof. The carrier comprising the antigen is exposed to a patient sample comprising antibodies such as diluted serum. If the sample comprises an antibody binding to the antigen, the resulting complex may be detected, for example, by incubation with a secondary antibody comprising a fluorescent dye such as fluorescein, followed by visual examination using fluorescence microscopy. Suitable reagents, devices and software packages are commercially available, for example, from EUROIMMUN™, Löbeck, Germany.

A sample subjected to a test determining only whether an autoantibody binding to NCDN is present, but in some embodiments, the diagnostic methods, tests, devices and the like may contemplate determining the presence of autoantibodies against a variety of antigens relating to neurological autoimmune disease or variants thereof, for example, selected from the group comprising Hu, Yo, Ri, CV2, PNMA1, PNMA2, DNER/Tr, ARHGAP26, ITPR1, ATP1A3, NBC1, CARPVIII, Zic4, Sox1, Ma, MAG, MP0, MBP, GAD65, amphiphysin, recoverin, GABA A receptor, GABA B receptor, glycine receptor, gephyrin, IgLON5, DPPX, aquaporin-4, MOG, NMDA receptor, AMPA receptors, GRM1, GRM5, LGI1, VGCC and mGluR1 and CASPR2, which antigens are for example, immobilized, for example, on a medical device such as a line blot. The diagnostically relevant markers ITPR1 (EP14003703.7), NBC1 (EP14003958.7) and ATP1A3, also referred to as alpha 3 subunit of human neuronal Na(+)/K(+) ATPase (EP14171561.5) have been described in the state of the art.

According to the teachings of the present disclosure, an antibody, for example, an autoantibody binding to the disclosed polypeptide used for the diagnosis of a disease is provided. The person skilled in the art is familiar with methods for purifying antibodies, for example, those described in Hermanson, G. T., Mallia, A. K., and Smith, P. K. (1992), Immobilized Affinity Ligand Techniques, San Diego: Academic Press. Briefly, an antigen binding specifically to the antibody of interest, which antigen is the disclosed polypeptide, is immobilized and used to purify, via affinity chromatography, the antibody of interest from an adequate source. A liquid sample comprising antibodies from a patient suffering from the neurological disorder identified by the inventors may be used as the source.

According to the disclosure, an antibody, for example, an autoantibody, is provided that is capable of binding specifically to the disclosed polypeptide. In an embodiment, the term "antibody," as used herein, refers to any immuglobulin-based binding moieties, for example, one comprising at least one immunoglobulin heavy chain and one immunoglobulin light chain, including, but not limited to monoclonal and polyclonal antibodies as well as variants of an antibody, in particular fragments, which binding moieties are capable of binding to the respective antigen, for example, binding specifically to it. In an embodiment, the term "binding specifically," as used herein, means that the binding is stronger than a binding reaction characterized by a dissociation constant of $1\times10\text{-}5$ M, $1\times10\text{-}7$ M, $1\times10\text{-}8$ M, $1\times10\text{-}9$ M, $1\times10\text{-}10$ M, $1\times10\text{-}11$ M, or $1\times10\text{-}12$ M, as determined by surface plasmon resonance using BIACORE™ equipment at 25° C. in PBS buffer at pH 7. The antibody may be isolated or in a mixture comprising further antibodies, polypeptides, metabolites, cells and the like. In case the antibody is an autoantibody, it may be part of an autoantibody preparation which is heterogeneous or may be a homogenous autoantibody, wherein a heterogeneous preparation comprises a plurality of different autoantibody species as obtainable by preparation from the sera of human donors, for example, by affinity chromatography using the immobilized antigen to purify any autoantibody capable of binding to said antigen. The antibody may be glycosylated or non-glycosylated. The person skilled in the art is familiar with methods that may be used for the identification, production and purification of antibodies and variants thereof, for examples, those described in EP 2 423 226 A2 and references therein. The antibody may be used as a diagnostic agent, by itself, or in combination, for example, in complex with the disclosed polypeptide.

The present disclosure provides a method for isolating an antibody, for example, an autoantibody, binding to the disclosed polypeptide, comprising the steps a) contacting a sample comprising the antibody with the disclosed polypeptide such that a complex is formed, b) isolating the complex formed in step a), c) dissociating the complex isolated in step b), and d) separating the antibody from the disclosed polypeptide. A sample from a patient suffering from the novel neurological disorder identified by the inventors may be used as the source of antibody. Alternatively the antibody may be a recombinant antibody. In some embodiments, the polypeptide is immobilized, for example, on the matrix of a column suitable for affinity chromatography or on a magnetic bead, since it is straightforward to separate the complex comprising the polypeptide and the antibody in step b) if such is the case. Subsequently, the antibody may be separated from the immobilized antigen in step c), for example, by eluting the antibody by addition of an excess of non-immobilized antigen or by adding an agent interfering with intramolecular interactions, for example, guanidinium chloride or sodium chloride at a high concentration, the latter if that electrostatic interactions are essential to maintain the complex. One or more washing steps may be included to increase the purity of the complex and the sensitivity and/or specificity of the assay whenever the complex is formed as part of detection or purification methods. The person skilled in the art is familiar with methods to carry out each of these steps. Suitable methods are described in the state of the art, for example, in the Handbooks "Affinity chromatography," "Strategies for Protein Purification" and "Antibody Purification" (2009/2010), published by GE Healthcare Life Sciences, and in in Philips, Terry, M., Analytical techniques in immunochemistry, 1992, Marcel Dekker, Inc.

The disclosure provides a pharmaceutical composition comprising the disclosed polypeptide, which composition may be suitable for administration to a subject, for example, a mammalian subject, for example, to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally," as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example, capsules, tablets and aqueous suspensions and solutions, for example, in sterile form. It may be used in a method of treatment of a disease, which method comprises administering an effective amount of the disclosed polypeptide to a subject. In an embodiment, the disclosure provides a vaccine comprising the disclosed polypeptide, optionally comprising an auxiliary agent such as an adjuvant or a buffer, and the use of the disclosed polypeptide for the preparation of a vaccine.

Within the scope of the present disclosure, a medical or diagnostic device comprising, for example, coated with the disclosed (auto)antibody and/or the disclosed polypeptide is provided. For example, such a medical or diagnostic device comprises the disclosed polypeptide in a form that allows contacting it with an aqueous solution, for example, the liquid human sample, in a straightforward manner. In particular, the disclosed polypeptide may be immobilized on the surface of a carrier, which carrier comprises, but is not limited to glass plates or slides, biochips, microtiter plates, beads, for example, magnetic beads, chromatography columns, membranes or the like. Exemplary medical devices include line blots, microplates and biochips. In addition to the disclosed polypeptide, the medical or diagnostic device may comprise additional polypeptides, for example, positive or negative controls or known other antigens binding to autoantibodies of diagnostic value, particularly those related to other diseases associated with one or more identical or similar symptoms.

The disclosed teachings provide a kit, for example, for diagnosing a disease. Such a kit may comprise instructions detailing how to use the kit and a means for contacting the disclosed polypeptide with a bodily fluid sample from a subject, for example, a human subject, for example, a line blot, wherein the disclosed polypeptide is immobilized on the line blot. Furthermore, the kit may comprise a positive control, for example, a batch of autoantibody or recombinant antibody known to bind to the disclosed polypeptide and a negative control, for example, a protein having no detectable affinity to the disclosed polypeptide such as bovine serum albumin. Finally, such a kit may comprise a standard solution of the antibody or antigen for preparing a calibration curve.

In an embodiment, the kit comprises a means for detecting an antibody, for example, an autoantibody, binding to the disclosed polypeptide, for example, by detecting a complex comprising the disclosed polypeptide and an antibody binding to the disclosed polypeptide. Such means may be an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, for example, a secondary antibody specific for mammalian IgG class antibodies. Alternatively, said means may be a crosslinking reagent chemically linking the antibody and the disclosed polypeptide, so the complex may be identified on account of its increased molecular weight, for example, by SDS PAGE followed by Coomassie staining or size-exclusion chromatography. A multitude of methods and means for detecting such a complex have been described in the state of the art, for example in Philips, Terry, M., Analytical techniques in immunochemistry, 1992, Marcel Dekker, Inc.

The disclosed polypeptide may be provided in the form of a cell comprising and/or expressing a nucleic acid encoding said polypeptide. If a nucleic acid comprising a sequence that encodes for the disclosed polypeptide or variant thereof is used, such a nucleic acid may be an unmodified nucleic acid. In an embodiment, the nucleic acid is a nucleic acid that, as such, does not occur in nature and comprises, compared to natural nucleic acid, at least one modification, for example, an isotopic content or chemical modifications, for example, a methylation, sequence modification, label or the like indicative of synthetic origin. In an embodiment, the nucleic acid is a recombinant nucleic acid or part or a nucleic acid, and is, in an embodiment, part of a vector, in which it may be functionally linked with a promoter that allows for expression, for example, overexpression of the nucleic acid.

In an embodiment, said nucleic acid is inside a cell capable of expressing it to the effect that the disclosed polypeptide or a variant thereof is made and, for example, routed to the surface of the cell. Said cell comprising the nucleic acid encoding the disclosed polypeptide may be used according to the present disclosure. The cell may be any kind of cell capable of expressing the nucleic acid, for example, a prokaryotic or eukaryotic cell. In an embodiment, the cell is a eukaryotic cell such as a yeast cell, a eukaryotic cell from a multicellular organism, for example, an insect cell, for example, a mammalian cell, for example, a mouse cell, and, for example, a human cell.

The person skilled in the art is familiar with methods used to synthesize, modify and amplify such a nucleic acid and to transfect cells using such a nucleic acid, for example, in a vector that allows for the transient or permanent maintenance or expression of the nucleic acid in the cell. The person skilled in the art is also familiar with a variety of suitable vectors, of which are commercially available, for example, from ORIGENE™. For example, a vector encoding for fusion constructs with a C-terminal GFP may be used. The cell may be of eukaryotic or prokaryotic origin and may be a mammalian cell, for example, a HEK293, CHO or COS-7 cell. The cell comprising the nucleic acid encoding for the disclosed polypeptide may be a recombinant cell or an isolated cell wherein the term "isolated" means that the cell is enriched such that, compared to the environment of the wild type of said cell, fewer cells of other differentiation or species or in fact no such other cells are present.

The disclosed teachings may not only be used for a diagnosis, but also for preventing or treating a disease, more specifically a method for preventing or treating a disease, comprising the steps a) reducing the concentration of autoantibodies binding to the disclosed polypeptide in the subject's blood and/or b) administering one or more immunosuppressive pharmaceutical substances, for example, selected from the group comprising rituximab, prednisone, methylprednisolone, cyclophosphamide, mycophenolate-mofetil, intravenous immunoglobulin, tacrolimus, cyclosporine, methotrexate, azathioprine and/or the pharmaceutical composition.

It will be obvious to those having skill in the art that many changes may be made to the details of the above-described embodiments without departing from the underlying principles of the disclosure. The scope of the present disclosure should, therefore, be determined only by the following claims.

The invention claimed is:

1. A method of detecting an autoantibody to Neurochondrin in a subject, the method comprising:
   contacting a bodily fluid sample isolated from a subject having cerebellar ataxia or cerebellitis with a polypeptide comprising Neurochondrin, wherein the polypeptide comprising Neurochondrin is recombinant and/or isolated, and binds specifically to autoantibodies binding to Neurochondrin, and
   detecting the presence or absence of the autoantibody to Neurochondrin in a complex with the polypeptide.

2. The method of claim 1, wherein the polypeptide is immobilized on a solid carrier.

3. The method of claim 1, wherein the polypeptide is provided in the form of an isolated cell comprising a nucleic acid encoding the polypeptide or in the form of an isolated tissue comprising the polypeptide.

4. The method of claim 1, wherein the subject is at least one of a human and a mammal.

5. A method of detecting a complex comprising an autoantibody bound to a polypeptide comprising Neurochondrin in a subject, the method comprising:
   obtaining a bodily fluid sample from a subject, wherein the subject has cerebellar ataxia or cerebellitis,
   contacting the bodily fluid sample from the subject with a polypeptide comprising Neurochondrin, wherein the polypeptide comprising Neurochondrin is recombinant and/or isolated, and binds specifically to autoantibodies binding to Neurochondrin, and
   detecting whether at least one complex comprising the autoantibody bound to the polypeptide is present in the bodily fluid sample.

6. The method of claim 5, wherein the polypeptide is immobilized on a solid carrier.

7. The method of claim 5, wherein detecting whether at least one complex comprising an autoantibody bound to the polypeptide is present in the bodily fluid sample comprises the use of a secondary antibody.

8. The method of claim 5, wherein detecting whether at least one complex comprising an autoantibody bound to the polypeptide is present in the bodily fluid sample comprises the use of at least one immunoassay technique selected from radioimmunoassay, western blot, line blot, enzyme-linked immunosorbent assay (ELISA), direct immunofluorescence, and indirect immunofluorescence.

9. The method of claim 5, wherein the bodily fluid is selected from the group comprising cerebrospinal fluid, whole blood, blood serum, lymph, interstitial fluid, and saliva.

10. The method of claim 5, wherein the polypeptide is provided in the form of an isolated cell comprising a nucleic acid encoding the polypeptide or in the form of an isolated tissue comprising the polypeptide.

11. The method of claim 5, wherein the subject is at least one of a human and a mammal.

\* \* \* \* \*

SEQUENCE LISTING

<160> NUMBER OF SEQ ID NOS: 9

<210> SEQ ID NO 1
<211> LENGTH: 2190
<212> TYPE: DNA
<213> ORGANISM: Homo sapiens

<400> SEQUENCE: 1

```
atgtcgtgtt gtgacctggc tgcggcggga cagttgggca aggcgagcat catggcctcg      60
gattgcgagc cagctctgaa ccaggcagag ggccgaaacc ccaccctgga gcgctacctg     120
ggagccctcc gtgaggccaa gaatgacagc gagcagtttg cagccctgct gctagtgacc     180
aaggcagtca aagcaggtga catagatgcc aaaactcggc ggcggatctt cgatgctgtc     240
ggcttcacct tccccaatcg tctcctgacc accaaggagg cgccggatgg ctgccctgac     300
catgttctgc gggctttggg tgtggccctg ctggcctgct tctgcagtga ccctgaactg     360
gccgcccatc cccaagtcct gaacaagatt cccattctta gcaccttcct cacagcccgg     420
ggggacccgg acgatgctgc ccgccgctcc atgattgatg acacctacca gtgcctgacg     480
gctgtagcag gcacacccag agggcctcgg cacctcattg ctggtggcac cgtgtctgcc     540
```

```
ctatgccagg catacctggg gcacggctat ggctttgacc aggccctggc actcctggtg      600
gggctgctgg ctgctgccga gacacagtgc tggaaggagg cggagcccga cctgctggcc      660
gtgttgcggg gcctcagtga ggatttccag aaagctgagg atgccagcaa gtttgagctc      720
tgccagctgc tgcccctctt tttgcccccg acaaccgtgc ccctgaatg ctaccgggat       780 ctgcaggccg ggctggcacg catcctggga agcaagctga gctcctggca gcgcaaccct      840
gcactgaagc tggcagcccg cctggcacac gcctgcggct ccgactggat cccggcgggc      900
agctccggga gcaagttcct ggccctgctg gtgaatctgg cgtgcgtgga agtgcggctg      960
gcactggagg agacgggcac ggaggtgaaa gaggatgtgt tgaccgcctg ctatgccctc     1020
atggagttgg ggatccagga atgcactcgc tgtgagcagt cactgcttaa ggagccacag     1080
aaggtgcagc tcgtgagcgt catgaaggag gccataggg ctgttatcca ctacctgctg      1140
caggtggggt cagagaagca gaaggagccc tttgtgtttg cctcggtgcg gatcctgggt     1200
gcctggctgg ccgaggagac ctcatccttg cgtaaggagg tgtgccagct gctgcccttc     1260
ctcgtccgct atgccaagac cctctacgag gaggccgagg aggccaatga ccttcccag      1320 caggtggcca acctggccat ccccccacc accccagggc ccacctggcc aggagacgct      1380
ctccggctcc tcctgcctgg ctggtgccac ctgaccgttg aagatgggcc ccgggagatc     1440
ctgatcaagg aagggggcccc ctcgcttctg tgcaagtatt tcctgcagca gtgggaactc    1500
acatcccctg ccacgacac ctcggtgctg cctgacagcg tggagattgg cctgcagacc      1560
tgctgccaca tcttcctcaa cctcgtggtc accgcaccgg ggctgatcaa gcgtgacgcc     1620
tgcttcacat ctctaatgaa caccctcatg acgtcgctac cagcactagt gcagcaacag     1680
ggaaggctgc ttctggctgc taatgtggcc accctgggc tcctcatggc ccggctcctt      1740
agcacctctc cagctcttca gggaacacca gcatcccgag ggttcttcgc agctgccatc     1800
ctcttcctat cacagtccca cgtggcgcgg gccaccccgg gctcagacca ggcagtgcta     1860
gccctgtccc ctgagtatga gggcatctgg gccgacctgc aggagctctg gttcctgggc     1920
atgcaggcct tcaccggctg tgtgcctctg ctgccctggc tggccccgc tgccctgcgc     1980 tcccgctggc cgcaggagct gctccagctg ctaggcagtg tcagcccaa ctctgtcaag     2040 cccgagatgg tggccgccta tcagggtgtc ctggtggagc tggcgcgggc caaccggctg     2100
tgccgggagg ccatgaggct gcaggcgggc gaggagacgg ccagccacta ccgcatggct     2160
gccttggagc agtgcctgtc agagccctga                                      2190
```

<210> SEQ ID NO 2
<211> LENGTH: 14
<212> TYPE: PRT
<213> ORGANISM: Homo sapiens

<400> SEQUENCE: 2

His Tyr Leu Leu Gln Val Gly Ser Glu Lys Gln Lys Glu Pro
1               5                   10

<210> SEQ ID NO 3
<211> LENGTH: 50
<212> TYPE: PRT
<213> ORGANISM: Homo sapiens

<400> SEQUENCE: 3

Met Ser Cys Cys Asp Leu Ala Ala Ala Gly Gln Leu Gly Lys Ala Ser
1               5                   10                  15

Ile Met Ala Ser Asp Cys Glu Pro Ala Leu Asn Gln Ala Glu Gly Arg
            20                  25                  30

Asn Pro Thr Leu Glu Arg Tyr Leu Gly Ala Leu Arg Glu Ala Lys Asn
            35                  40                  45

Asp Ser
    50

<210> SEQ ID NO 4
<211> LENGTH: 19
<212> TYPE: PRT
<213> ORGANISM: Homo sapiens

<400> SEQUENCE: 4

Glu Glu Thr Ala Ser His Tyr Arg Met Ala Ala Leu Glu Gln Cys Leu
1               5                   10                  15

Ser Glu Pro

<210> SEQ ID NO 5
<211> LENGTH: 150
<212> TYPE: PRT
<213> ORGANISM: Homo sapiens

<400> SEQUENCE: 5

Met Ser Cys Cys Asp Leu Ala Ala Ala Gly Gln Leu Gly Lys Ala Ser
1               5                   10                  15

Ile Met Ala Ser Asp Cys Glu Pro Ala Leu Asn Gln Ala Glu Gly Arg
            20                  25                  30

Asn Pro Thr Leu Glu Arg Tyr Leu Gly Ala Leu Arg Glu Ala Lys Asn
            35                  40                  45

Asp Ser Glu Gln Phe Ala Ala Leu Leu Leu Val Thr Lys Ala Val Lys
    50                  55                  60

Ala Gly Asp Ile Asp Ala Lys Thr Arg Arg Arg Ile Phe Asp Ala Val
65                  70                  75                  80

Gly Phe Thr Phe Pro Asn Arg Leu Leu Thr Thr Lys Glu Ala Pro Asp
                85                  90                  95

Gly Cys Pro Asp His Val Leu Arg Ala Leu Gly Val Ala Leu Leu Ala
            100                 105                 110

Cys Phe Cys Ser Asp Pro Glu Leu Ala Ala His Pro Gln Val Leu Asn
            115                 120                 125

Lys Ile Pro Ile Leu Ser Thr Phe Leu Thr Ala Arg Gly Asp Pro Asp
        130                 135                 140

Asp Ala Ala Arg Arg Ser
145                 150

<210> SEQ ID NO 6
<211> LENGTH: 150
<212> TYPE: PRT
<213> ORGANISM: Homo sapiens

<400> SEQUENCE: 6

Met Ile Asp Asp Thr Tyr Gln Cys Leu Thr Ala Val Ala Gly Thr Pro
1               5                   10                  15

Arg Gly Pro Arg His Leu Ile Ala Gly Gly Thr Val Ser Ala Leu Cys
            20                  25                  30

Gln Ala Tyr Leu Gly His Gly Tyr Gly Phe Asp Gln Ala Leu Ala Leu
            35                  40                  45

Leu Val Gly Leu Leu Ala Ala Ala Glu Thr Gln Cys Trp Lys Glu Ala
        50                  55                  60

Glu Pro Asp Leu Leu Ala Val Leu Arg Gly Leu Ser Glu Asp Phe Gln
65                  70                  75                  80

Lys Ala Glu Asp Ala Ser Lys Phe Glu Leu Cys Gln Leu Leu Pro Leu
                85                  90                  95

Phe Leu Pro Pro Thr Thr Val Pro Pro Glu Cys Tyr Arg Asp Leu Gln
            100                 105                 110

Ala Gly Leu Ala Arg Ile Leu Gly Ser Lys Leu Ser Ser Trp Gln Arg
        115                 120                 125

Asn Pro Ala Leu Lys Leu Ala Ala Arg Leu Ala His Ala Cys Gly Ser
    130                 135                 140

Asp Trp Ile Pro Ala Gly
145                 150

<210> SEQ ID NO 7
<211> LENGTH: 150
<212> TYPE: PRT
<213> ORGANISM: Homo sapiens

<400> SEQUENCE: 7

Ser Ser Gly Ser Lys Phe Leu Ala Leu Leu Val Asn Leu Ala Cys Val
1               5                   10                  15

Glu Val Arg Leu Ala Leu Glu Glu Thr Gly Thr Glu Val Lys Glu Asp
                20                  25                  30

Val Val Thr Ala Cys Tyr Ala Leu Met Glu Leu Gly Ile Gln Glu Cys
            35                  40                  45

Thr Arg Cys Glu Gln Ser Leu Leu Lys Glu Pro Gln Lys Val Gln Leu
        50                  55                  60

Val Ser Val Met Lys Glu Ala Ile Gly Ala Val Ile His Tyr Leu Leu
65                  70                  75                  80

Gln Val Gly Ser Glu Lys Gln Lys Glu Pro Phe Val Phe Ala Ser Val
                85                  90                  95

Arg Ile Leu Gly Ala Trp Leu Ala Glu Glu Thr Ser Ser Leu Arg Lys
            100                 105                 110

Glu Val Cys Gln Leu Leu Pro Phe Leu Val Arg Tyr Ala Lys Thr Leu
        115                 120                 125

Tyr Glu Glu Ala Glu Glu Ala Asn Asp Leu Ser Gln Gln Val Ala Asn
    130                 135                 140

Leu Ala Ile Ser Pro Thr
145                 150

<210> SEQ ID NO 8
<211> LENGTH: 150
<212> TYPE: PRT
<213> ORGANISM: Homo sapiens

<400> SEQUENCE: 8

Thr Pro Gly Pro Thr Trp Pro Gly Asp Ala Leu Arg Leu Leu Leu Pro
1               5                   10                  15

Gly Trp Cys His Leu Thr Val Glu Asp Gly Pro Arg Glu Ile Leu Ile
                20                  25                  30

Lys Glu Gly Ala Pro Ser Leu Leu Cys Lys Tyr Phe Leu Gln Gln Trp
            35                  40                  45

Glu Leu Thr Ser Pro Gly His Asp Thr Ser Val Leu Pro Asp Ser Val
        50                  55                  60

Glu Ile Gly Leu Gln Thr Cys Cys His Ile Phe Leu Asn Leu Val Val
65                  70                  75                  80

-continued

```
Thr Ala Pro Gly Leu Ile Lys Arg Asp Ala Cys Phe Thr Ser Leu Met
             85                  90                  95

Asn Thr Leu Met Thr Ser Leu Pro Ala Leu Val Gln Gln Gln Gly Arg
             100                 105                 110

Leu Leu Leu Ala Ala Asn Val Ala Thr Leu Gly Leu Leu Met Ala Arg
         115                 120                 125

Leu Leu Ser Thr Ser Pro Ala Leu Gln Gly Thr Pro Ala Ser Arg Gly
     130                 135                 140

Phe Phe Ala Ala Ala Ile
145             150

<210> SEQ ID NO 9
<211> LENGTH: 129
<212> TYPE: PRT
<213> ORGANISM: Homo sapiens

<400> SEQUENCE: 9

Leu Phe Leu Ser Gln Ser His Val Ala Arg Ala Thr Pro Gly Ser Asp
1               5                   10                  15

Gln Ala Val Leu Ala Leu Ser Pro Glu Tyr Glu Gly Ile Trp Ala Asp
            20                  25                  30

Leu Gln Glu Leu Trp Phe Leu Gly Met Gln Ala Phe Thr Gly Cys Val
        35                  40                  45

Pro Leu Leu Pro Trp Leu Ala Pro Ala Ala Leu Arg Ser Arg Trp Pro
    50                  55                  60

Gln Glu Leu Leu Gln Leu Leu Gly Ser Val Ser Pro Asn Ser Val Lys
65                  70                  75                  80

Pro Glu Met Val Ala Ala Tyr Gln Gly Val Leu Val Glu Leu Ala Arg
            85                  90                  95

Ala Asn Arg Leu Cys Arg Glu Ala Met Arg Leu Gln Ala Gly Glu Glu
            100                 105                 110

Thr Ala Ser His Tyr Arg Met Ala Ala Leu Glu Gln Cys Leu Ser Glu
            115                 120                 125

Pro
```